(12) United States Patent
Grelsamer

(10) Patent No.: US 6,740,057 B2
(45) Date of Patent: May 25, 2004

(54) EXTERNAL DEVICE DIMINISHING ODDS OF PATIENT DISENGAGING HIP REPLACEMENT

(76) Inventor: Ronald P. Grelsamer, 35 E. 85th St., New York, NY (US) 10028

( * ) Notice: Subject to any disclaimer, the term of this patent is extended or adjusted under 35 U.S.C. 154(b) by 0 days.

(21) Appl. No.: 09/905,060

(22) Filed: Jul. 13, 2001

(65) Prior Publication Data

US 2003/0013999 A1 Jan. 16, 2003

(51) Int. Cl.$^7$ .............................. A61F 5/00; A61G 15/00
(52) U.S. Cl. ........................... 602/24; 128/845; 602/19
(58) Field of Search ................ 602/23, 5, 16, 602/24, 20, 19; 128/123.1, 877, 878, 882, 845, 846, 41–42, 53–54, 849

(56) References Cited

U.S. PATENT DOCUMENTS

| | | | |
|---|---|---|---|
| 2,753,864 A | | 7/1956 | Weidemann, Jr. |
| 2,889,830 A | | 6/1959 | Raymond |
| 3,938,510 A | * | 2/1976 | Gerber .................. 602/22 |
| 4,481,941 A | | 11/1984 | Rolfes |
| 4,633,863 A | * | 1/1987 | Filips et al. ............. 128/846 |
| 4,736,477 A | * | 4/1988 | Moore ..................... 128/892 |
| 4,905,678 A | | 3/1990 | Cumins et al. |
| 5,195,944 A | * | 3/1993 | Schlogel ................ 602/21 |
| 5,230,699 A | * | 7/1993 | Grasinger .............. 602/22 |
| 5,286,251 A | | 2/1994 | Thompson et al. |
| 5,452,729 A | * | 9/1995 | Bergsbaken et al. ........ 128/849 |
| 5,456,659 A | * | 10/1995 | Gildersleeve et al. ......... 602/15 |
| 5,476,442 A | * | 12/1995 | Madej ....................... 602/20 |
| 5,584,072 A | | 12/1996 | Kim et al. |
| 5,620,412 A | | 4/1997 | Modglin |
| 5,651,743 A | * | 7/1997 | Stephan et al. ............. 473/450 |
| 5,681,267 A | * | 10/1997 | Molino et al. .............. 602/19 |
| 5,790,981 A | | 8/1998 | Bzoch |
| 5,830,168 A | | 11/1998 | Finnell et al. |
| 5,840,050 A | | 11/1998 | Lerman |
| 5,848,983 A | * | 12/1998 | Basaj et al. ................ 602/22 |
| 5,928,175 A | | 7/1999 | Tanaka |
| 5,947,915 A | * | 9/1999 | Thibodo, Jr. .................. 602/5 |
| 6,039,706 A | * | 3/2000 | Bolla et al. .................... 602/5 |
| 6,245,034 B1 | * | 6/2001 | Bennett et al. ............... 602/16 |
| 6,293,918 B1 | * | 9/2001 | Wang ........................ 128/878 |
| 6,506,957 B1 | * | 1/2003 | Himmelsbach et al. ....... 602/41 |

\* cited by examiner

*Primary Examiner*—Michael A. Brown
*Assistant Examiner*—Fenn C Mathew
(74) *Attorney, Agent, or Firm*—John P. White; Cooper & Dunham LLP

(57) ABSTRACT

Device for restricting movement of a bone joint comprises a rigid material sandwiched between two foam layers, the pad having a surface adapted to be fastened to a user by adhesive material, the pad having a generally rectangular shape defined by two generally parallel sides, a top and a bottom, and having two pad portions desired by a crease line extending between the two sides, the two pad portions forming a determined angle less than 180 degrees with respect to each other.

15 Claims, 4 Drawing Sheets

EXTERNAL DEVICE DIMINISHING ODDS OF PATIENT DISENGAGING HIP REPLACEMENT

BACKGROUND OF THE INVENTION

The present invention relates to a bone joint anti-dislocation device, and more particularly to an anti-dislocation device for a hip joint.

One of the known complications of hip replacement surgery is a hip dislocation, which is an extremely painful condition whereby the hip "ball" pops out of its socket. The hip can pop out the back ("posterior dislocation") or the front ("anterior dislocation").

An early if not the first device designed to avoid this dislocation was a hip spica cast, a bulky plaster cast device which could not be removed even for washing or scratching. This was applied to patients who had dislocated or were felt to be at great risk for dislocation.

A subsequent device, considered an improvement, is a so-called "spica brace" also known as a "hip abduction brace". This brace consists of a wide plastic belt that wraps around a person's waist and is connected to a plastic sleeve which wraps around the person's thigh. A hinge located on the side of the device connects the two parts, locking them at a fixed prescribed angle. Because the device is locked and constraining, a person wearing the brace is intentionally limited in how much they can bend and straighten the hip. Thus the person is unable to put the hip in a position that will make it pop out. This position is usually that of hip "flexion" (bending) to 90° or more. The brace also prevents the hip from "adducting", i.e. prevents the leg from being moved towards the other leg.

A major disadvantage of this device is that people do not like it because it can not easily be worn under a patient's normal clothing, it is bulky, it is unsightly and it chafes.

To prevent (posterior) dislocations, hip flexion is the only motion that needs to be controlled. Though adduction can be a contributing factor, it is relatively unimportant as long as hip flexion is controlled. Therefore, the bulky "hip spica brace" represents overkill.

SUMMARY OF THE INVENTION

According to one aspect of the invention, a device for restricting movement of a joint is provided comprising a pad adapted to be fastened to a user across a joint, said pad having two portions restricted from forming an angle with respect to each other less than a determined angle, said determined angle being less than 180 degrees.

According to another aspect of the invention, a device for restricting movement of a joint is provided comprising a pad made of rigid material sandwiched between two foam layers, said pad having a surface adapted to be fastened to a user by adhesive material, said pad having a generally rectangular shape defined by two generally parallel sides, a top and a bottom, and having two portions defined by a crease line extending between the two sides, said two portions forming a determined angle less than 180 degrees with respect to each other.

According to another aspect of the invention, a device for restricting movement of a joint is provided comprising a rigid pad having two portions connected by a hinge, said hinge adapted to be fastened to a user across a joint, and restricting movement of the two portions less than a determined angle, said determined angle being less than 180 degrees, and preferably within a pre-determined range of two angles, both being less than 180 degress.

DETAILED DESCRIPTION OF THE PREFERRED EMBODIMENT

According to one aspect of the invention, a device for restricting movement of a joint is provided comprising a pad adapted to be fastened to a user across a joint, said pad having two portions restricted from forming an angle with respect to each other less than a determined angle, said determined angle being less than 180 degrees.

According to another aspect of the invention, a device for restricting movement of a joint is provided comprising a pad made of rigid material sandwiched between two foam layers, said pad having a surface adapted to be fastened to a user by adhesive material, said pad having a generally rectangular shape defined by two generally parallel sides, a top and a bottom, and having two portions defined by a crease line extending between the two sides, said two portions forming a determined angle less than 180 degrees with respect to each other.

The pad preferably comprises a rigid material selected from the group consisting of metal and plastic.

The pad preferably comprises two foam type layers sandwiching the rigid material.

The pad preferably comprises a surface adapted to be fastened to a user by adhesive selected from the group consisting of tape and glue.

The device may include two straps for fastening the device to a user.

The two portions may be connected by a hinge, said hinge restricting the movement of the two portions less than said determined angle. The hinge may restrict movement outside the range of two angles both being less than 180 degrees.

The two portions may be defined by a crease line in the pad.

The pad preferably has a generally rectangular shape defined by two generally parallel sides, a top and a bottom.

The two portions are preferably defined by a crease line extending between the two sides and intersecting the sides at an acute angle.

The rigid material may be selected from the group consisting of metal and plastic.

The device may include an adhesive surface for fastening the device to a user.

According to another aspect of the invention, a device for restricting movement of a joint is provided comprising a rigid pad adapted to be fastened to a user across a joint, and having two portions connected by a hinge, said hinge restricting movement of the two portions less than a determined angle, said determined angle being less than 180 degrees.

The rigid material may be selected from the group consisting of metal and plastic.

The hinge preferably restricts the movement of the two portions within a range of two angles both being less than 180 degrees.

Figure 1:
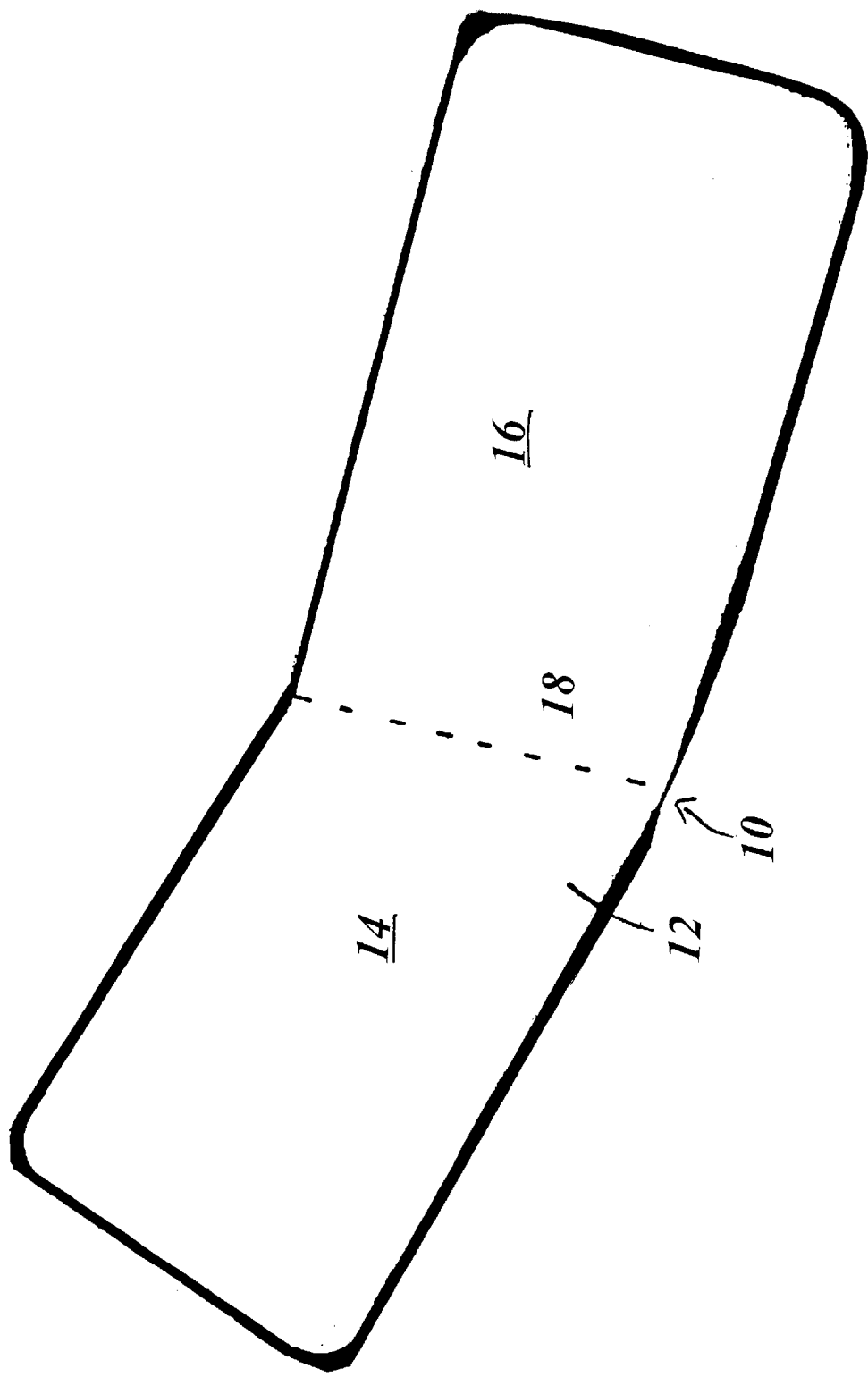
FIG. 1 is a perspective view of a device according to the invention.
Figure 2:
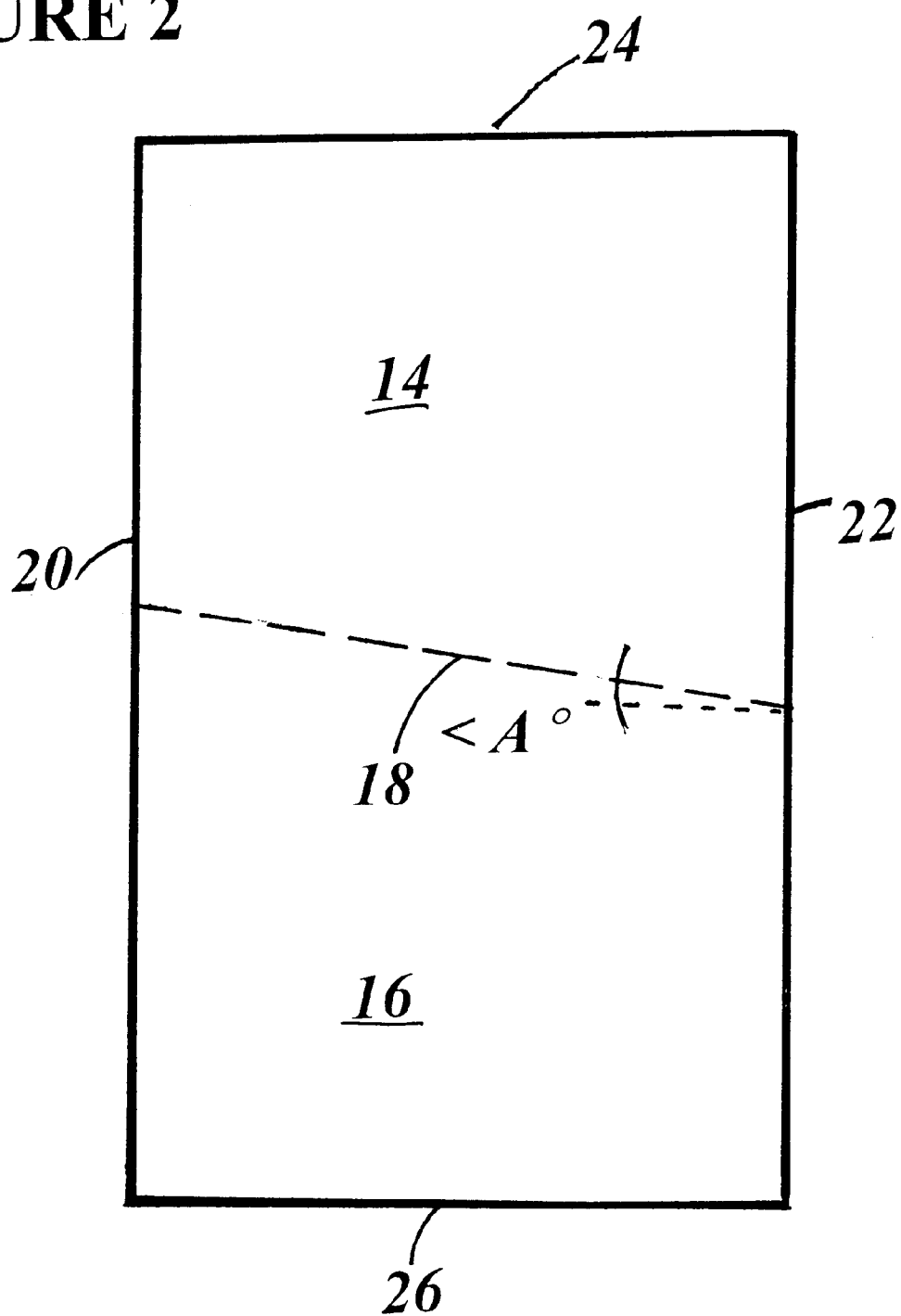
FIG. 2 is a top plan view of the embodiment of FIG. 1.

Referring to FIG. 1, a device 10 is shown comprising a pad 12 formed of two portions 14 and 16. The portions are defined by a crease line 18 (shown dotted) which goes from one side edge of the pad to the opposite side edge as seen in FIG. 2, the pad has a generally rectangular shape with parallel sides edges 20 and 22 and a top edge 24 and bottom edge 26. The crease line extends from one side edge to the other side edge, and forms an angle A relative to a line normal to the side edge, which angle less than 90 degrees. In the preferred embodiment, the angle A is patient dependent and can be on the order of about 20 degrees, for example.

Figure 3:
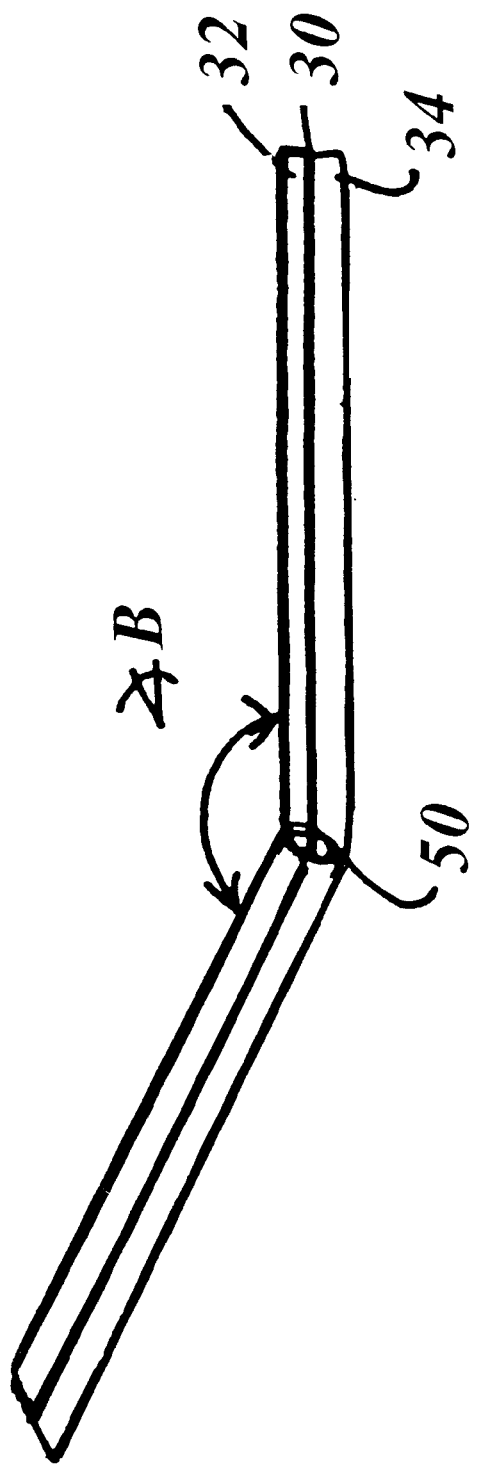
FIG. 3 is a side view of the embodiment of FIG. 1.

As shown in FIG. 3, the device 10 is formed of a plate of rigid material 30, such as metal or plastic. As used herein, the term "rigid" means substantially non deformable by further bending of the two portions at the crease line when worn by a typical human user. The rigid material is sandwiched by two foam layers 32 and 34 of bio-compatible material.

The device of FIGS. 1 and 2 may be used across the hip joint is intended to be worn by a user by adhesion to the front groin area, positioned so that the crease line is parallel to the inquinal ligament rotation axis of the upper leg and torso. The crease line will thus extend from the crotch or groin area to upwardly and outwardly to the outer hip area. The device shown in FIG. 2, wherein the crease line is slanted or angled upwardly from right to left, is intended to be worn on the top of the right thigh. For a left thigh the crease line would be slanted or angled upwardly from left to right, and would be the mirror image of the device shown in FIG. 2.

Due to the crease line, the two portions form an angle B (see FIG. 3) with respect to each other less than 180 degrees and in the preferred embodiment the angle is about 150 degrees.

Figure 4:
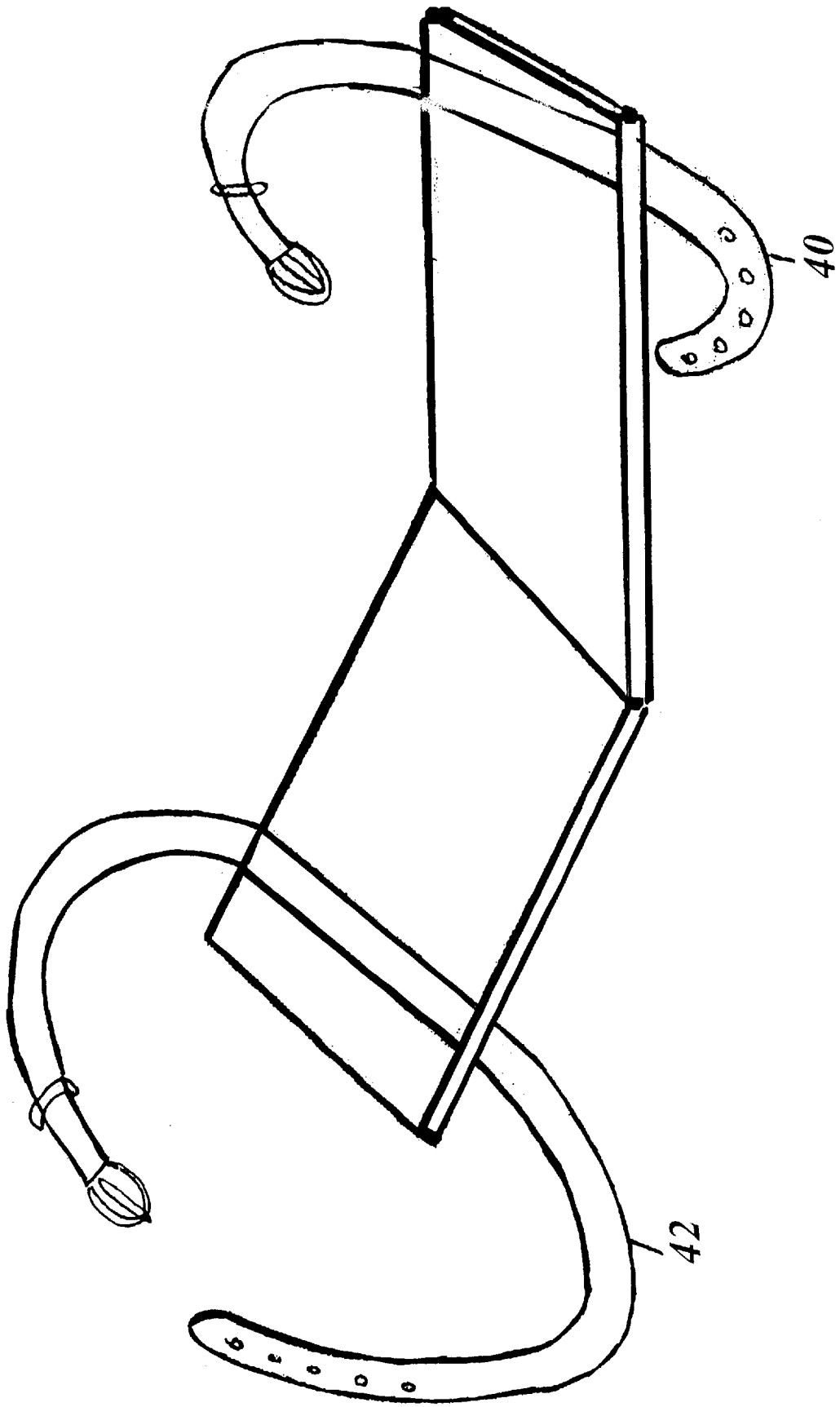
FIG. 4 is a perspective view of the anti-dislocation pad with straps.

The device is fastened to the user by adhesive such as double sided tape (e.g. McConnell tape) or other adhesive. As shown in FIG. 4 the device can alternatively or additionally be fastened by two straps, or belts 40 and 42, the lower strap to be worn around a user's upper thigh and the upper strap to be worn around the user's waist.

As shown in FIG. 3, the two pad portions may be connected by a hinge 50, which hinge has a hinge pivot axis substantially the same as the crease line as shown in FIGS. 1 and 2. The hinge may restrict movement of the two pad portions relative to each other between a range of two angles, both angles being less than 180 degrees. This hinge variation allows at least a range of movement between the two angles.

The device can be provided in a number of different angles to allow semi-custom fit for different patients. A more custom fit may be obtained by providing a medical practitioner with a flat plate formed of a material which enables deformation upon heating for example, with instructions for heating the plate and bending the material to the desired angle to form the crease line.

Once fitted to the patient, the patient will feel resistance as soon as he or she tries to bend the hip joint. This feedback will limit the possibility of the hip being placed in a poor position. The feedback also provides a patient with a reminder of the permitted range of movement, to thereby maintain hip precautions.

To be fitted, the patient stands with the affected hip flexed (bent) just enough to keep his or her ball of the foot on the ground. The angle between the lower abdomen and upper thigh is measured. The patient is provided with a pad whose bent angle corresponds to that measurement.

Although one embodiment has been shown and described, numerous variations and modifications will readily occur to those skilled in the art. The scope of the invention is defined only by way of the appended claims.

I claim:

1. A device for restricting otherwise normal movement of a hip joint comprising a pad having an adhesive material on a surface to fasten to a user across a joint, said pad having side edges and two opposed faces on opposite surfaces of the pad, said pad having a crease line extending between the side edges and intersecting the side edges at an acute angle, said crease line defining two portions restricted from forming an angle with respect to each other less than a determined angle, said determined angle being less than 180 degrees, said adhesive for attaching a face of each of the two portions to the front of a user at the hip joint so that the crease line is aligned with the hip joint when the two portions are adhesed to the user at opposite sides of the hip joint.

2. The device according to claim 1, wherein the pad comprises a rigid material selected from the group consisting of metal and plastic.

3. The device according to claim 2, wherein the pad comprises two foam layers sandwiching the rigid material.

4. The device according to claim 1, wherein the pad comprises a surface to be fastened to a user by adhesive selected from the group consisting of tape and glue.

5. The device according to claim 1, further comprising two straps for fastening the device to a user.

6. The device according to claim 1, wherein the two portions are connected by a hinge, said hinge restricting the movement of the two portions less than said determined angle.

7. The device according to claim 6, wherein the hinge is restricted from movement outside the range of two angles both being less than 180 degrees.

8. The device according to claim 1, wherein the pad has a generally rectangular shape defined by two generally parallel sides, a top and a bottom.

9. A device for restricting otherwise normal movement of a hip joint, comprising a rigid material sandwiched between two foam layers, said pad having a surface adapted to be fastened to a user by adhesive material, said pad having a generally rectangular shape defined by two generally parallel sides, a top and a bottom, and having two portions defined by a crease line extending between the two sides and intersecting the side edges at an acute angle, said two portions forming a determined angle less than 180 degrees with respect to each other, said adhesive for attaching a face of each of the two portions to the front of a user at the hip joint so that the crease line is aligned with the hip joint when the two portions are adhesed to the user at opposite sides of the hip joint.

10. The device according to claim 9, wherein the rigid material is selected from the group consisting of metal and plastic.

11. A device for restricting otherwise normal movement of a hip joint comprising a rigid pad having side edges and two opposed faces on opposite surfaces of the pad, said pad having a hinge line extending between the side edges and intersecting the side edges at an acute angle, said pad having an adhesive material on one of said surfaces and having two portions connected by a hinge, both of said two portions adapted to be fastened to a user across a joint with the adhesive, and said hinge restricting movement of the two portions less than a determined angle, said determined angle being less than 180 degrees.

12. The device according to claim 11, wherein the rigid material is selected from the group consisting of metal and plastic.

13. The device according to claim 11, wherein the hinge restricts the movement of the two portions within a range of two angles both being less than 180 degrees.

14. A device for restricting otherwise normal movement of a hip joint comprising a pad to be fastened to a user across a joint, said pad having side edges and two opposed faces on opposite surfaces of the pad, said pad having a crease line extending between the side edges and intersecting the side edges at an acute angle, said crease line defining two substantially planer and rigid portions restricted from forming an angle with respect to each other less than a determined angle, said determined angle being less than 180 degrees, said adhesive for attaching a face of each of the two portions to the front of a user at the hip joint so that the crease line is aligned with the hip joint when the two portions are adhesed to the user at opposite sides of the hip joint.

15. A device for restricting otherwise normal movement of a joint, comprising a rigid pad having side edges and two opposed faces on opposite surfaces of the pad, said pad having a crease line extending between the side edges and intersecting the side edges at an acute angle, said crease line defining two portions connected by a hinge, said hinge adapted to be fastened to a user across a joint, and restricting movement of the two portions relative to each other to a range between two angles both being less than 180 degrees, and adhesive for attaching a face of each of the two portions to the front of a user at the hip joint so that the crease line is aligned with the hip joint when the two portions are adhesed to the user at opposite sides of the hip joint.

* * * * *